(12) United States Patent
Gladieux

(10) Patent No.: US 11,890,034 B1
(45) Date of Patent: *Feb. 6, 2024

(54) COLLET FOR A POLYAXIAL SCREW ASSEMBLY

(71) Applicant: SeaSpine Orthopedics Corporation, Carlsbad, CA (US)

(72) Inventor: Corey Noel Gladieux, Vista, CA (US)

(73) Assignee: SeaSpine Orthopedics Corporation, Carlsbad, CA (US)

( * ) Notice: Subject to any disclaimer, the term of this patent is extended or adjusted under 35 U.S.C. 154(b) by 997 days.

This patent is subject to a terminal disclaimer.

(21) Appl. No.: 16/715,763

(22) Filed: Dec. 16, 2019

Related U.S. Application Data

(63) Continuation of application No. 15/730,400, filed on Oct. 11, 2017, now Pat. No. 10,507,043.

(51) Int. Cl.
*A61B 17/70* (2006.01)
*A61B 17/86* (2006.01)

(52) U.S. Cl.
CPC ...... *A61B 17/7035* (2013.01); *A61B 17/8605* (2013.01); *A61B 17/8685* (2013.01); *A61B 17/7032* (2013.01)

(58) Field of Classification Search
CPC ...... A61B 17/70–7056; A61B 17/7001; A61B 17/7032; A61B 17/7034; A61B 17/7035; A61B 17/7037; A61B 17/7038; A61B 17/704; A61B 17/7041; A61B 17/7043; A61B 17/7046

See application file for complete search history.

(56) References Cited

U.S. PATENT DOCUMENTS

| | | | |
|---|---|---|---|
| 2,699,774 | A | 1/1955 | Livingston |
| 4,653,481 | A | 3/1987 | Howland et al. |
| 4,719,905 | A | 1/1988 | Steffee |
| 4,805,602 | A | 2/1989 | Puno et al. |
| 4,950,269 | A | 8/1990 | Gaines, Jr. |
| 5,053,036 | A | 10/1991 | Perren et al. |
| 5,085,660 | A | 2/1992 | Lin |
| 5,108,395 | A | 4/1992 | Laurain |
| 5,112,332 | A | 5/1992 | Cozad et al. |
| 5,116,334 | A | 5/1992 | Cozad et al. |

(Continued)

FOREIGN PATENT DOCUMENTS

| | | |
|---|---|---|
| WO | 0019923 | 4/2000 |
| WO | 0152758 | 7/2001 |

OTHER PUBLICATIONS

PCT/US2004/010319 International Preliminary Report on Patentability and Written Opinion dated Oct. 14, 2005, pp. 1-4.

(Continued)

*Primary Examiner* — Lynnsy M Summitt
(74) *Attorney, Agent, or Firm* — Dinsmore & Shohl LLP

(57) ABSTRACT

An apparatus and method related to a collet for a spinal screw are described herein. In some embodiments, such an apparatus includes a screw, a movable head comprising a top portion and a bottom portion, a concave interior larger than a screw head, a connecting rod, a locking element screw, and a collet interposed between the screw head and the concave interior of the movable head, where the collet comprises a flexible hinge, and where the collet reduces axial compression force transferred from the set screw to the screw head.

16 Claims, 11 Drawing Sheets

(56) References Cited

U.S. PATENT DOCUMENTS

| | | |
|---|---|---|
| 5,152,303 A | 10/1992 | Allen |
| 5,154,719 A | 10/1992 | Cotrel |
| 5,181,917 A | 1/1993 | Rogozinski |
| 5,196,013 A | 3/1993 | Harms et al. |
| 5,207,678 A | 5/1993 | Harms et al. |
| 5,261,911 A | 11/1993 | Carl |
| 5,281,223 A | 1/1994 | Ray |
| 5,324,290 A | 6/1994 | Zdeblick et al. |
| 5,330,473 A | 7/1994 | Howland |
| 5,380,325 A | 1/1995 | Lahille et al. |
| 5,382,248 A | 1/1995 | Jacobson et al. |
| 5,403,314 A | 4/1995 | Currier |
| 5,443,467 A | 8/1995 | Biedermann et al. |
| 5,466,237 A | 11/1995 | Byrd, III et al. |
| 5,474,555 A | 12/1995 | Puno et al. |
| 5,480,401 A | 1/1996 | Navas |
| 5,486,176 A | 1/1996 | Hildebrand et al. |
| 5,501,684 A | 3/1996 | Schlapfer et al. |
| 5,549,608 A | 8/1996 | Errico et al. |
| 5,554,157 A | 9/1996 | Errico et al. |
| 5,584,834 A | 12/1996 | Errico et al. |
| 5,586,984 A | 12/1996 | Errico et al. |
| 5,591,165 A | 1/1997 | Jackson |
| 5,591,235 A | 1/1997 | Kuslich |
| 5,601,552 A | 2/1997 | Cotrel |
| 5,615,965 A | 4/1997 | Saurat et al. |
| 5,620,443 A | 4/1997 | Gertzbein et al. |
| 5,624,442 A | 4/1997 | Mellinger et al. |
| 5,669,911 A | 9/1997 | Errico et al. |
| 5,672,176 A | 9/1997 | Biedermann et al. |
| 5,681,319 A | 10/1997 | Biedermann et al. |
| 5,683,391 A | 11/1997 | Boyd |
| 5,690,630 A | 11/1997 | Errico et al. |
| 5,713,900 A | 2/1998 | Benzel et al. |
| 5,716,356 A | 2/1998 | Biedermann et al. |
| 5,725,527 A | 3/1998 | Biedermann et al. |
| 5,728,098 A | 3/1998 | Sherman et al. |
| 5,733,285 A | 3/1998 | Errico et al. |
| 5,738,685 A | 4/1998 | Halm et al. |
| 5,752,957 A | 5/1998 | Ralph et al. |
| 5,782,833 A | 7/1998 | Halder |
| 5,797,911 A | 8/1998 | Sherman et al. |
| 5,800,435 A | 9/1998 | Errico et al. |
| 5,817,094 A | 10/1998 | Errico et al. |
| 5,863,293 A | 1/1999 | Richelsoph |
| 5,879,350 A | 3/1999 | Sherman et al. |
| 5,882,350 A | 3/1999 | Ralph et al. |
| 5,885,286 A | 3/1999 | Sherman et al. |
| 5,888,221 A | 3/1999 | Gelbard |
| 5,891,145 A | 4/1999 | Morrison et al. |
| 5,910,142 A | 6/1999 | Tatar |
| 5,925,047 A | 7/1999 | Errico et al. |
| 5,954,725 A | 9/1999 | Sherman et al. |
| 5,964,760 A | 10/1999 | Richelsoph |
| 5,989,254 A | 11/1999 | Katz |
| 5,997,539 A | 12/1999 | Errico et al. |
| 6,010,503 A | 1/2000 | Richelsoph et al. |
| 6,017,344 A | 1/2000 | Errico et al. |
| 6,019,759 A | 2/2000 | Rogozinski |
| 6,022,350 A | 2/2000 | Ganem |
| 6,048,343 A | 4/2000 | Mathis et al. |
| 6,050,997 A | 4/2000 | Mullane |
| 6,053,917 A | 4/2000 | Sherman et al. |
| 6,063,090 A | 5/2000 | Schlapfer |
| 6,074,391 A | 6/2000 | Metz-Stavenhagen |
| 6,090,111 A | 7/2000 | Nichols |
| 6,113,601 A | 9/2000 | Tatar |
| 6,132,430 A | 10/2000 | Wagner |
| 6,132,432 A | 10/2000 | Richelsoph |
| 6,132,434 A | 10/2000 | Sherman et al. |
| 6,146,383 A | 11/2000 | Studer et al. |
| 6,183,473 B1 | 2/2001 | Ashman |
| 6,187,005 B1 | 2/2001 | Brace et al. |
| 6,206,879 B1 | 3/2001 | Marnay et al. |
| 6,210,376 B1 | 4/2001 | Grayson |
| 6,214,006 B1 | 4/2001 | Metz-Stavenhagen |
| 6,214,012 B1 | 4/2001 | Karpman et al. |
| RE37,161 E | 5/2001 | Michelson et al. |
| 6,226,548 B1 | 5/2001 | Foley et al. |
| 6,248,105 B1 | 6/2001 | Schlapfer et al. |
| 6,254,602 B1 | 7/2001 | Justis |
| 6,273,888 B1 | 8/2001 | Justis |
| 6,280,442 B1 | 8/2001 | Barker et al. |
| 6,280,443 B1 | 8/2001 | Gu et al. |
| 6,287,311 B1 | 9/2001 | Sherman et al. |
| 6,302,888 B1 | 10/2001 | Mellinger et al. |
| 6,309,391 B1 | 10/2001 | Crandall et al. |
| 6,355,040 B1 | 3/2002 | Richelsoph et al. |
| 6,361,535 B2 | 3/2002 | Jackson |
| RE37,665 E | 4/2002 | Ralph et al. |
| 6,368,321 B1 | 4/2002 | Jackson |
| 6,371,957 B1 | 4/2002 | Amrein et al. |
| 6,375,657 B1 | 4/2002 | Doubler et al. |
| 6,413,257 B1 | 7/2002 | Lin et al. |
| 6,416,515 B1 | 7/2002 | Wagner |
| 6,440,137 B1 | 8/2002 | Horvath et al. |
| 6,454,768 B1 | 9/2002 | Jackson |
| 6,454,773 B1 | 9/2002 | Sherman et al. |
| 6,458,132 B2 | 10/2002 | Choi |
| 6,471,705 B1 | 10/2002 | Biedermann |
| 6,475,218 B2 | 11/2002 | Gournay et al. |
| 6,485,491 B1 | 11/2002 | Farris et al. |
| 6,485,494 B1 | 11/2002 | Haider |
| 6,488,681 B2 | 12/2002 | Martin et al. |
| 6,537,276 B2 | 3/2003 | Metz-Stavenhagen |
| 6,540,748 B2 | 4/2003 | Lombardo |
| 6,547,790 B2 | 4/2003 | Harkey, III et al. |
| 6,554,832 B2 | 4/2003 | Shluzas |
| 6,554,834 B1 | 4/2003 | Crozet et al. |
| 6,565,565 B1 | 5/2003 | Yuan et al. |
| 6,565,567 B1 | 5/2003 | Haider |
| 6,582,436 B2 | 6/2003 | Schlapfer et al. |
| 6,595,992 B1 | 7/2003 | Wagner et al. |
| 6,613,050 B1 | 9/2003 | Wagner et al. |
| 6,623,485 B2 | 9/2003 | Doubler et al. |
| 6,626,906 B1 | 9/2003 | Young |
| 6,626,908 B2 | 9/2003 | Cooper et al. |
| 6,641,586 B2 | 11/2003 | Varieur |
| 6,652,526 B1 | 11/2003 | Arafiles |
| 6,660,004 B2 | 12/2003 | Barker et al. |
| 6,660,006 B2 | 12/2003 | Markworth et al. |
| 6,689,137 B2 | 2/2004 | Reed |
| 6,692,500 B2 | 2/2004 | Reed |
| 6,695,843 B2 | 2/2004 | Biedermann et al. |
| 6,702,817 B2 | 3/2004 | Beger et al. |
| 6,706,045 B2 | 3/2004 | Lin et al. |
| 6,716,214 B1 | 4/2004 | Jackson |
| 6,723,100 B2 | 4/2004 | Biedermann et al. |
| 6,730,092 B2 | 5/2004 | Songer |
| 6,736,820 B2 | 5/2004 | Biedermann et al. |
| 6,740,086 B2 | 5/2004 | Richelsoph |
| 6,755,829 B1 | 6/2004 | Bono et al. |
| 6,755,835 B2 | 6/2004 | Schultheiss et al. |
| 6,770,075 B2 | 8/2004 | Howland |
| 6,783,527 B2 | 8/2004 | Drewry et al. |
| 6,786,907 B2 | 9/2004 | Lange |
| 6,800,078 B2 | 10/2004 | Reed |
| 6,800,079 B2 | 10/2004 | Reed |
| 6,835,196 B2 | 12/2004 | Biedermann et al. |
| 6,837,889 B2 | 1/2005 | Shluzas |
| 6,843,791 B2 | 1/2005 | Serhan |
| 6,858,030 B2 | 2/2005 | Martin et al. |
| 6,858,031 B2 | 2/2005 | Morrison et al. |
| 6,869,432 B2 | 3/2005 | Schlapfer et al. |
| 6,869,433 B2 | 3/2005 | Glascott |
| 6,887,242 B2 | 5/2005 | Doubler et al. |
| 6,896,677 B2 | 5/2005 | Lin |
| 6,905,500 B2 | 6/2005 | Jeon et al. |
| 6,918,911 B2 | 7/2005 | Biedermann et al. |
| 6,951,561 B2 | 10/2005 | Warren et al. |
| 6,964,664 B2 | 11/2005 | Fried et al. |
| 6,964,666 B2 | 11/2005 | Jackson |
| 6,974,460 B2 | 12/2005 | Carbone et al. |
| 6,981,973 B2 | 1/2006 | McKinley |

(56) References Cited

U.S. PATENT DOCUMENTS

| | | |
|---|---|---|
| 7,018,379 B2 | 3/2006 | Drewry et al. |
| 7,022,122 B2 | 4/2006 | Amrein et al. |
| RE39,089 E | 5/2006 | Ralph et al. |
| 7,087,057 B2 | 8/2006 | Konieczynski |
| 7,141,051 B2 | 11/2006 | Janowski et al. |
| 7,163,539 B2 | 1/2007 | Abdelgany et al. |
| 7,186,255 B2 | 3/2007 | Baynham et al. |
| 7,211,086 B2 | 5/2007 | Biedermann et al. |
| 7,223,268 B2 | 5/2007 | Biedermann |
| 7,250,052 B2 | 7/2007 | Landry et al. |
| 7,264,621 B2 | 9/2007 | Coates et al. |
| 7,303,562 B2 | 12/2007 | Cavagna et al. |
| 7,314,467 B2 | 1/2008 | Howland |
| 7,316,684 B1 | 1/2008 | Baccelli et al. |
| 7,322,979 B2 | 1/2008 | Crandall et al. |
| 7,335,202 B2 | 2/2008 | Matthis et al. |
| 7,377,923 B2 | 5/2008 | Purcell et al. |
| 7,445,627 B2 | 11/2008 | Hawkes et al. |
| 7,476,239 B2 | 1/2009 | Jackson |
| 7,530,992 B2 | 5/2009 | Biedermann et al. |
| 7,604,655 B2 | 10/2009 | Warnick |
| D603,503 S | 11/2009 | Kriska et al. |
| D603,504 S | 11/2009 | Kriska et al. |
| D603,505 S | 11/2009 | Kriska et al. |
| D603,506 S | 11/2009 | Kriska et al. |
| D603,507 S | 11/2009 | Kriska et al. |
| D603,508 S | 11/2009 | Kriska et al. |
| D603,509 S | 11/2009 | Kriska et al. |
| D603,510 S | 11/2009 | Kriska et al. |
| D603,511 S | 11/2009 | Kriska et al. |
| D603,961 S | 11/2009 | Kriska et al. |
| D603,962 S | 11/2009 | Kriska et al. |
| D603,963 S | 11/2009 | Kriska et al. |
| D603,964 S | 11/2009 | Kriska et al. |
| 7,625,394 B2 | 12/2009 | Molz, IV et al. |
| 7,635,380 B2 | 12/2009 | Zucherman et al. |
| 7,678,137 B2 | 3/2010 | Butler et al. |
| 7,686,835 B2 | 3/2010 | Warnick |
| 7,691,129 B2 | 4/2010 | Felix |
| 7,691,132 B2 | 4/2010 | Landry et al. |
| 7,717,941 B2 | 5/2010 | Petit |
| 7,744,635 B2 | 6/2010 | Sweeny et al. |
| 7,766,944 B2 | 8/2010 | Metz-Stavenhagen |
| 7,776,040 B2 | 8/2010 | Markworth et al. |
| 7,780,706 B2 | 8/2010 | Marino et al. |
| 7,833,252 B2 | 11/2010 | Justis et al. |
| 7,875,065 B2 | 1/2011 | Jackson |
| 7,892,257 B2 | 2/2011 | Abdelgany |
| 7,914,558 B2 | 3/2011 | Landry et al. |
| 7,931,676 B2 | 4/2011 | Veldman et al. |
| 7,931,678 B2 | 4/2011 | Konieczynski et al. |
| 7,951,172 B2 | 5/2011 | Chao et al. |
| 8,002,806 B2 | 8/2011 | Justis |
| 8,012,186 B2 | 9/2011 | Pham et al. |
| 8,016,862 B2 | 9/2011 | Felix |
| 8,021,397 B2 | 9/2011 | Farris et al. |
| 8,038,701 B2 | 10/2011 | Rock et al. |
| 8,048,124 B2 | 11/2011 | Chin |
| 8,048,129 B2 | 11/2011 | Forton et al. |
| 8,075,594 B2 | 12/2011 | Purcell |
| 8,092,494 B2 | 1/2012 | Butler et al. |
| 8,097,020 B2 | 1/2012 | Markworth et al. |
| 8,100,946 B2 | 1/2012 | Strausbaugh et al. |
| 8,118,842 B2 | 2/2012 | Klyce et al. |
| 8,137,387 B2 * | 3/2012 | Garamszegi ....... A61B 17/7037 606/270 |
| 8,157,846 B2 * | 4/2012 | Randol ............. A61B 17/7037 606/279 |
| 8,167,910 B2 | 5/2012 | Nilsson |
| 8,167,912 B2 | 5/2012 | Jacofsky et al. |
| 8,167,913 B2 | 5/2012 | Albert et al. |
| 8,197,517 B1 | 6/2012 | Lab et al. |
| 8,221,472 B2 | 7/2012 | Peterson |
| 8,337,530 B2 | 12/2012 | Hestad et al. |
| 8,398,682 B2 | 3/2013 | Jackson et al. |
| 8,449,577 B2 | 5/2013 | Kloss et al. |
| 8,556,938 B2 | 10/2013 | Jackson |
| 8,628,558 B2 | 1/2014 | Harvey et al. |
| 8,632,571 B2 | 1/2014 | Kraus |
| 8,845,693 B2 | 9/2014 | Smith |
| 8,951,294 B2 | 2/2015 | Gennari |
| 8,986,349 B1 | 3/2015 | German |
| 9,084,634 B1 | 7/2015 | Lab |
| 9,486,246 B2 | 11/2016 | Biedermann |
| 9,707,014 B1 | 7/2017 | Lab et al. |
| 10,159,519 B2 | 12/2018 | Biedermann |
| 10,194,950 B2 | 2/2019 | Felix |
| 10,507,043 B1 | 12/2019 | Gladieux |
| 2001/0001119 A1 | 5/2001 | Lombardo |
| 2002/0010467 A1 | 1/2002 | Cooper et al. |
| 2002/0022842 A1 | 2/2002 | Horvath et al. |
| 2002/0026193 A1 | 2/2002 | Barker et al. |
| 2002/0035366 A1 | 3/2002 | Walder et al. |
| 2002/0058942 A1 | 5/2002 | Biedermann et al. |
| 2002/0082602 A1 | 6/2002 | Biedermann et al. |
| 2002/0091386 A1 | 7/2002 | Martin et al. |
| 2002/0120272 A1 | 8/2002 | Yuan |
| 2002/0133154 A1 | 9/2002 | Saint Martin |
| 2002/0138076 A1 | 9/2002 | Biedermann et al. |
| 2002/0143341 A1 | 10/2002 | Biedermann et al. |
| 2002/0151900 A1 | 10/2002 | Glascott |
| 2002/0183748 A1 | 12/2002 | Martin et al. |
| 2003/0004512 A1 | 1/2003 | Farris et al. |
| 2003/0023243 A1 | 1/2003 | Biedermann et al. |
| 2003/0032957 A1 | 2/2003 | McKinley |
| 2003/0073996 A1 | 4/2003 | Doubler et al. |
| 2003/0073997 A1 | 4/2003 | Doubler et al. |
| 2003/0083657 A1 | 5/2003 | Drewry et al. |
| 2003/0100896 A1 | 5/2003 | Biedermann et al. |
| 2003/0100904 A1 | 5/2003 | Biedermann |
| 2003/0125741 A1 | 7/2003 | Biedermann et al. |
| 2003/0149431 A1 | 8/2003 | Varieur |
| 2003/0158552 A1 | 8/2003 | Jeon et al. |
| 2003/0187439 A1 | 10/2003 | Biedermann et al. |
| 2003/0187442 A1 | 10/2003 | Richelsoph et al. |
| 2003/0199873 A1 | 10/2003 | Richelsoph |
| 2004/0030337 A1 | 2/2004 | Alleyne et al. |
| 2004/0097933 A1 | 5/2004 | Lourdel et al. |
| 2004/0102781 A1 | 5/2004 | Jeon |
| 2004/0116929 A1 | 6/2004 | Barker |
| 2004/0138660 A1 | 7/2004 | Serhan |
| 2004/0138662 A1 | 7/2004 | Landry et al. |
| 2004/0143265 A1 | 7/2004 | Landry et al. |
| 2004/0153077 A1 | 8/2004 | Biedermann et al. |
| 2004/0158247 A1 | 8/2004 | Sitiso et al. |
| 2004/0172022 A1 | 9/2004 | Landry et al. |
| 2004/0172025 A1 | 9/2004 | Drewry et al. |
| 2004/0181224 A1 | 9/2004 | Biedermann et al. |
| 2004/0186473 A1 | 9/2004 | Cournoyer et al. |
| 2004/0186474 A1 | 9/2004 | Matthis et al. |
| 2004/0193160 A1 | 9/2004 | Richelsoph |
| 2004/0225289 A1 | 11/2004 | Biedermann et al. |
| 2004/0230192 A1 | 11/2004 | Graf |
| 2004/0236330 A1 | 11/2004 | Purcell et al. |
| 2004/0243126 A1 | 12/2004 | Carbone et al. |
| 2004/0249378 A1 | 12/2004 | Saint Martin et al. |
| 2004/0249380 A1 | 12/2004 | Glascott |
| 2004/0260283 A1 | 12/2004 | Wu et al. |
| 2004/0260284 A1 | 12/2004 | Parker |
| 2004/0267264 A1 | 12/2004 | Konieczynski et al. |
| 2005/0010218 A1 | 1/2005 | Dalton |
| 2005/0010219 A1 | 1/2005 | Dalton |
| 2005/0033296 A1 | 2/2005 | Bono et al. |
| 2005/0033298 A1 | 2/2005 | Hawkes et al. |
| 2005/0038430 A1 | 2/2005 | McKinley |
| 2005/0049588 A1 | 3/2005 | Jackson |
| 2005/0049589 A1 | 3/2005 | Jackson |
| 2005/0055026 A1 | 3/2005 | Biedermann et al. |
| 2005/0070899 A1 | 3/2005 | Doubler et al. |
| 2005/0070901 A1 | 3/2005 | David |
| 2005/0080415 A1 | 4/2005 | Keyer et al. |
| 2005/0080420 A1 | 4/2005 | Farris et al. |
| 2005/0085812 A1 | 4/2005 | Sherman et al. |
| 2005/0119658 A1 | 6/2005 | Ralph et al. |

(56) References Cited

U.S. PATENT DOCUMENTS

| | | |
|---|---|---|
| 2005/0131410 A1 | 6/2005 | Lin |
| 2005/0137594 A1 | 6/2005 | Doubler et al. |
| 2005/0154389 A1 | 7/2005 | Selover et al. |
| 2005/0154391 A1 | 7/2005 | Doherty et al. |
| 2005/0171542 A1 | 8/2005 | Biedermann et al. |
| 2005/0177154 A1 | 8/2005 | Moumene et al. |
| 2005/0187548 A1 | 8/2005 | Butler et al. |
| 2005/0187555 A1 | 8/2005 | Biedermann |
| 2005/0192571 A1 | 9/2005 | Abdelgany |
| 2005/0192573 A1 | 9/2005 | Abdelgany et al. |
| 2005/0192580 A1 | 9/2005 | Dalton |
| 2005/0192589 A1 | 9/2005 | Raymond et al. |
| 2005/0203515 A1 | 9/2005 | Doherty et al. |
| 2005/0203516 A1 | 9/2005 | Biedermann et al. |
| 2005/0216003 A1 | 9/2005 | Biedermann et al. |
| 2005/0228379 A1 | 10/2005 | Jackson |
| 2005/0228382 A1 | 10/2005 | Richelsoph |
| 2005/0240180 A1 | 10/2005 | Vienney et al. |
| 2005/0251139 A1 | 11/2005 | Roh |
| 2005/0261687 A1 | 11/2005 | Garamszegi et al. |
| 2005/0267472 A1 | 12/2005 | Biedermann et al. |
| 2005/0277923 A1 | 12/2005 | Sweeney |
| 2005/0277928 A1 | 12/2005 | Boschert |
| 2005/0277931 A1 | 12/2005 | Sweeney et al. |
| 2005/0283157 A1 | 12/2005 | Coates et al. |
| 2005/0288671 A1 | 12/2005 | Yuan |
| 2006/0036242 A1 | 2/2006 | Nilsson et al. |
| 2006/0036244 A1 | 2/2006 | Spitler et al. |
| 2006/0036252 A1 | 2/2006 | Baynham et al. |
| 2006/0036260 A1 | 2/2006 | Runco et al. |
| 2006/0052783 A1 | 3/2006 | Dant et al. |
| 2006/0052784 A1 | 3/2006 | Dant et al. |
| 2006/0058788 A1 | 3/2006 | Hammer et al. |
| 2006/0074419 A1 | 4/2006 | Taylor et al. |
| 2006/0084979 A1 | 4/2006 | Jackson |
| 2006/0084980 A1 | 4/2006 | Melkent et al. |
| 2006/0084981 A1 | 4/2006 | Shluzas |
| 2006/0084993 A1 | 4/2006 | Landry et al. |
| 2006/0129149 A1 | 6/2006 | Iott et al. |
| 2006/0142761 A1 | 6/2006 | Landry et al. |
| 2006/0149245 A1 | 7/2006 | Sweeney |
| 2006/0200128 A1 | 9/2006 | Mueller |
| 2006/0235389 A1 | 10/2006 | Albert et al. |
| 2007/0055235 A1 | 3/2007 | Janowski et al. |
| 2007/0090238 A1 | 4/2007 | Justis |
| 2007/0118123 A1 | 5/2007 | Strausbaugh et al. |
| 2007/0270813 A1* | 11/2007 | Garamszegi ....... A61B 17/7032 606/278 |
| 2008/0021473 A1 | 1/2008 | Butler et al. |
| 2008/0097441 A1 | 4/2008 | Hayes et al. |
| 2008/0132953 A1 | 6/2008 | Carbone et al. |
| 2008/0161859 A1 | 7/2008 | Nilsson |
| 2008/0183223 A1 | 7/2008 | Jeon et al. |
| 2008/0243189 A1 | 10/2008 | Purcell et al. |
| 2008/0262556 A1 | 10/2008 | Jacofsky et al. |
| 2008/0312655 A1 | 12/2008 | Kirschman et al. |
| 2009/0062914 A1 | 3/2009 | Marino |
| 2009/0105716 A1 | 4/2009 | Barrus |
| 2009/0105770 A1 | 4/2009 | Berrevoets et al. |
| 2009/0118772 A1 | 5/2009 | Diederich et al. |
| 2010/0063545 A1 | 3/2010 | Richelsoph |
| 2010/0087873 A1 | 4/2010 | Null et al. |
| 2010/0125302 A1 | 5/2010 | Hammill et al. |
| 2010/0152787 A1 | 6/2010 | Walsh |
| 2010/0204735 A1 | 8/2010 | Gephart et al. |
| 2010/0249837 A1 | 9/2010 | Seme et al. |
| 2011/0054536 A1 | 3/2011 | Elsebaie et al. |
| 2011/0098747 A1 | 4/2011 | Donner et al. |
| 2011/0152949 A1 | 6/2011 | Biedermann |
| 2011/0178558 A1 | 7/2011 | Barry |
| 2011/0178559 A1 | 7/2011 | Barry |
| 2011/0196431 A1 | 8/2011 | Chao et al. |
| 2011/0257690 A1 | 10/2011 | Rezach |
| 2012/0109218 A1 | 5/2012 | Farris |
| 2013/0090693 A1 | 4/2013 | Strausbaugh et al. |
| 2014/0121703 A1 | 5/2014 | Jackson |
| 2017/0172630 A1* | 6/2017 | Biedermann ...... A61B 17/7002 |

OTHER PUBLICATIONS

PCT/US2004/010319 International Search Report dated Oct. 14, 2004, p. 1.

PCT/US2004/010319 Written Opinion of the International Search Authority dated Oct. 14, 2004, pp. 1-3.

* cited by examiner

COLLET FOR A POLYAXIAL SCREW ASSEMBLY

FIELD

Embodiments of the invention pertain to spinal surgery.

BACKGROUND

Surgery, whether of the spine or other areas of the body, is often complex and routinely involves the need for highly experienced medical staff, in addition to well-designed and well-manufactured implants, made to exacting specifications. Often the implants take the form of various types of hardware. At times, this hardware includes polyaxial pedicle screws that may allow angulation in various degrees of freedom between the movable screw head and the screw itself. Such screws may have a spherical head which is attached to a bone screw, and is captured somewhere within the moveable head. Conventionally, a bone screw head may be pushed through a lower opening of a screw head by excess compression force transferred from a locking element. This excess compression force may result in failure of the screw head/bone screw interface, and may result in a loss of fixation of the bone screw. The described invention aims to limit the compression force from the locking element to prevent this failure and provide a more circumferential lock between the bone screw/screw head interface.

Summary

An apparatus and method related to a collet for a spinal screw are described herein. In one aspect an apparatus, may include: a screw, including a shaft and a screw head fixedly attached with the shaft, where the screw head further comprises a portion of a sphere; a movable head including a top portion and a bottom portion, a concave interior larger than the screw head, and being movable with respect to the screw head; a connecting rod; a locking element, capable of engaging the movable head and creating an axial compression force thereon the connecting rod; and a collet interposed between the screw head and the concave interior of the movable head, where the collet comprises a top portion capable of contacting said connecting rod and at least one flexible hinge, where the collet limits the axial compression force transferred from the locking element to the screw head by deforming outwards at the at least one flexible hinge until contact is made with the concave interior of the moveable head.

In some embodiments, the flexible hinge may extend from the top end of the collet and for a distance spaced from the bottom end of the collet, and opposite the flexible hinge is an open slot extending vertically from the top end of the collet to the bottom end of the collet. In other embodiments, the flexible hinge may extend from the top end of the collet to the bottom end of the collet, and opposite the flexible hinge is an open slot extending vertically from the top end of the collet to the bottom end of the collet.

In some embodiment, the collet may further include an internal surface and an external surface, and where the flexible hinge has a larger radius than the external surface of the collet. In some embodiments, the flexible hinge may include a concave tab extending outward from the external surface of the collet. In other embodiments, the flexible hinge may be perpendicular to the cradle capable of receiving the connecting rod.

In some embodiments, the movable head further may include one or more tracks capable of receiving the flexible hinge of the collet. In other embodiments, the one or more tracks may be vertical tracks. In still other embodiments, the one or more tracks may be circumferential tracks located between the plurality of threads.

In another aspect a collet for a polyaxial screw assembly is disclosed, and may include: a top end configured to receive a connecting rod; a bottom end configured to interface with a screw head fixedly attached with a shaft of a screw; a flexible hinge extending in a direction; and an open slot extending in a direction from the top end to the bottom end and located opposite the flexible hinge, where the open slot creates a discontinuous circumference.

In some embodiments, the flexible hinge may extend from the top end of the collet and for a distance spaced from the bottom end of the collet. In other embodiments, the flexible hinge may extend from the top end of the collet to the bottom end of the collet. In still other embodiments, the flexible hinge may include a concave tab extending outward from an external surface of the collet. In still other embodiments, the flexible hinge may be at a position that is perpendicular to a longitudinal axis of a cradle of the top end capable of receiving the connecting rod.

In yet another aspect, a method of inserting a collet into a movable head is disclosed. The method including: obtaining a collet and a movable head, wherein the collet comprises a flexible hinge and wherein the movable head comprises a first track that traverses from adjacent a top portion of the movable head to a bottom portion of the movable head; inserting the collet into a first track of the movable head in a compressed configuration; moving the collet along at least the first track of the movable head in the compressed configuration; and positioning the collet into an uncompressed configuration within said moveable head.

In some embodiments, the movable head further may comprise a second track intersecting the first track, where the second track is substantially circumferential and the first track is traverse to the second track. In other embodiments, moving the collet may include rotating the collet from a first orientation to a second orientation within the second track.

In some embodiments, the first track may be a channel and the second track may be a channel, and where the step of moving the collet along at least the first track of the movable head in the compressed configuration may include sliding the flexible hinge in the first track then the second track. In other embodiments, the first track may be a channel and the step of moving the collet along at least the first track of the movable head in the compressed configuration may include sliding the flexible hinge within the first channel of the first track.

In some embodiments, the movable head may further comprise an open slot extending from a top end to a bottom end of the collet, where the open slot creates a discontinuous circumference.

BRIEF DESCRIPTION OF THE FIGURES

Embodiments are further described in the following illustrations.

FIG. 8A illustrates a collet in an initial installation position; FIG. 8B illustrates a collet in an engaged position; FIG. 8C illustrates a collet in a rotated position; FIG. 8D illustrates a collet in an installed position.

DETAILED DESCRIPTION

Figure 1:
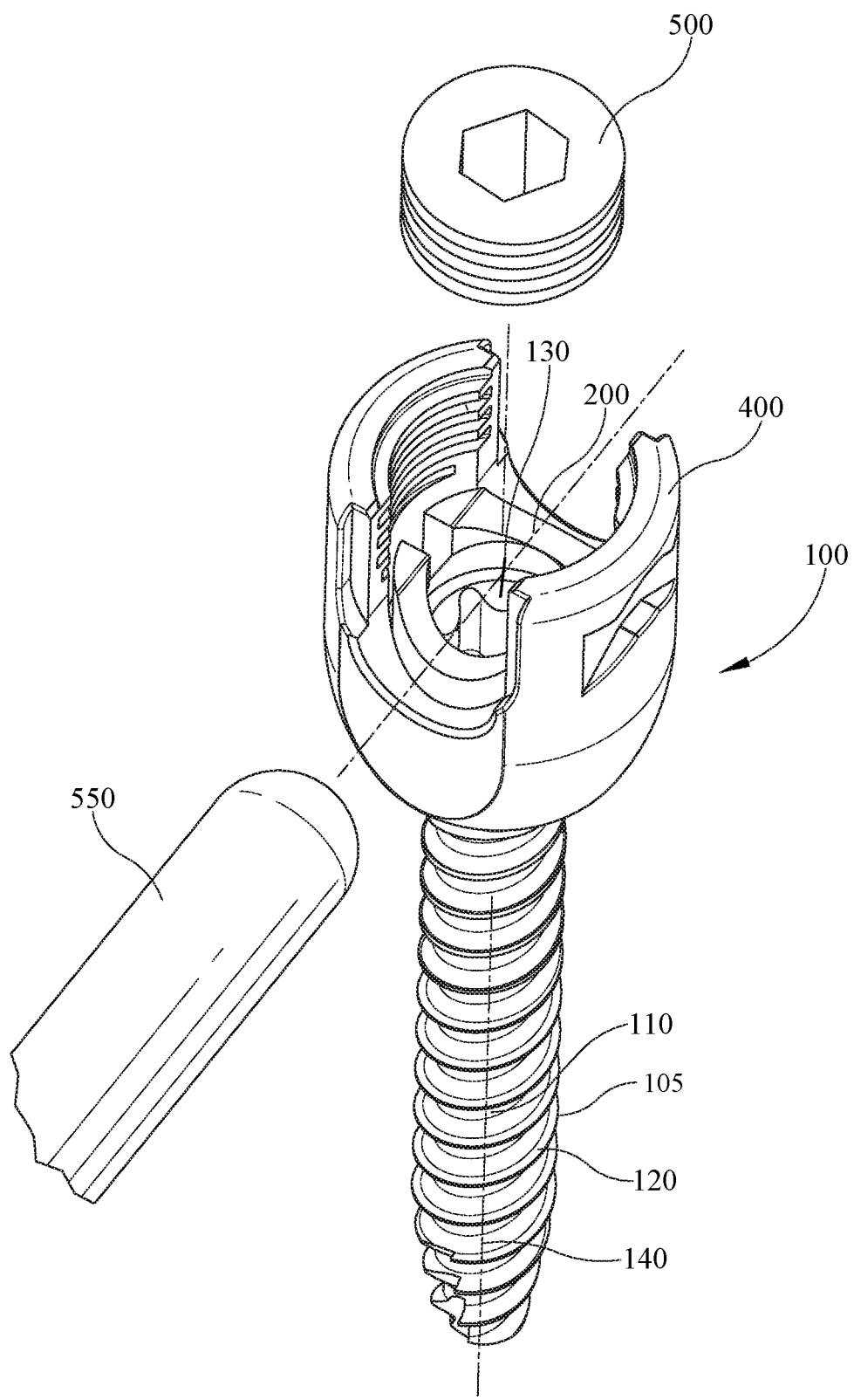
FIG. 1 is a perspective view of an embodiment of an apparatus described herein.

Embodiments will be further understood with reference to various Figures. With reference to FIG. 1, an embodiment of a portion of an apparatus 100 that provides a screw 105 that may possess a shaft 110, and a screw head 130 that may be integral with or attached to the shaft 110. The screw head 130 may be a portion of a sphere or have a spheroidal shape. The apparatus may further be provided with a collet 200 that may fit around all or a portion of the screw head 130. The apparatus may further have a movable head 400, 600, which will in turn contain the collet 200.

Screw

Screw 100 may possess threads 120 around shaft 110. Screw 100 may have a longitudinal axis 140. The longitudinal axis 140 generally extends through the center of the screw 100 along its length. In the vicinity of longitudinal axis 140, the screw shaft 110 may be either solid (as illustrated) or alternatively may be hollow, with the empty central region being available for other purposes as may be desired. The screw 100, including the screw head 130, may be axisymmetric about longitudinal axis 140.

Locking Element

The apparatus may further be provided with a locking element. A locking element may be any element capable of applying vertical force to lock the rod to the moveable screw head. A locking element may be, for example, a set screw 500 that may have an external thread 540 that may engage with an internal thread, or set of internal threads of a movable head (described in detail herein). It is further possible that there could be provided timing features marked on any of the nearby parts for indicating the optimal place to begin engagement of the set screw thread 540 and the internal thread, or set of threads of the movable head.

Collet

Figure 2:
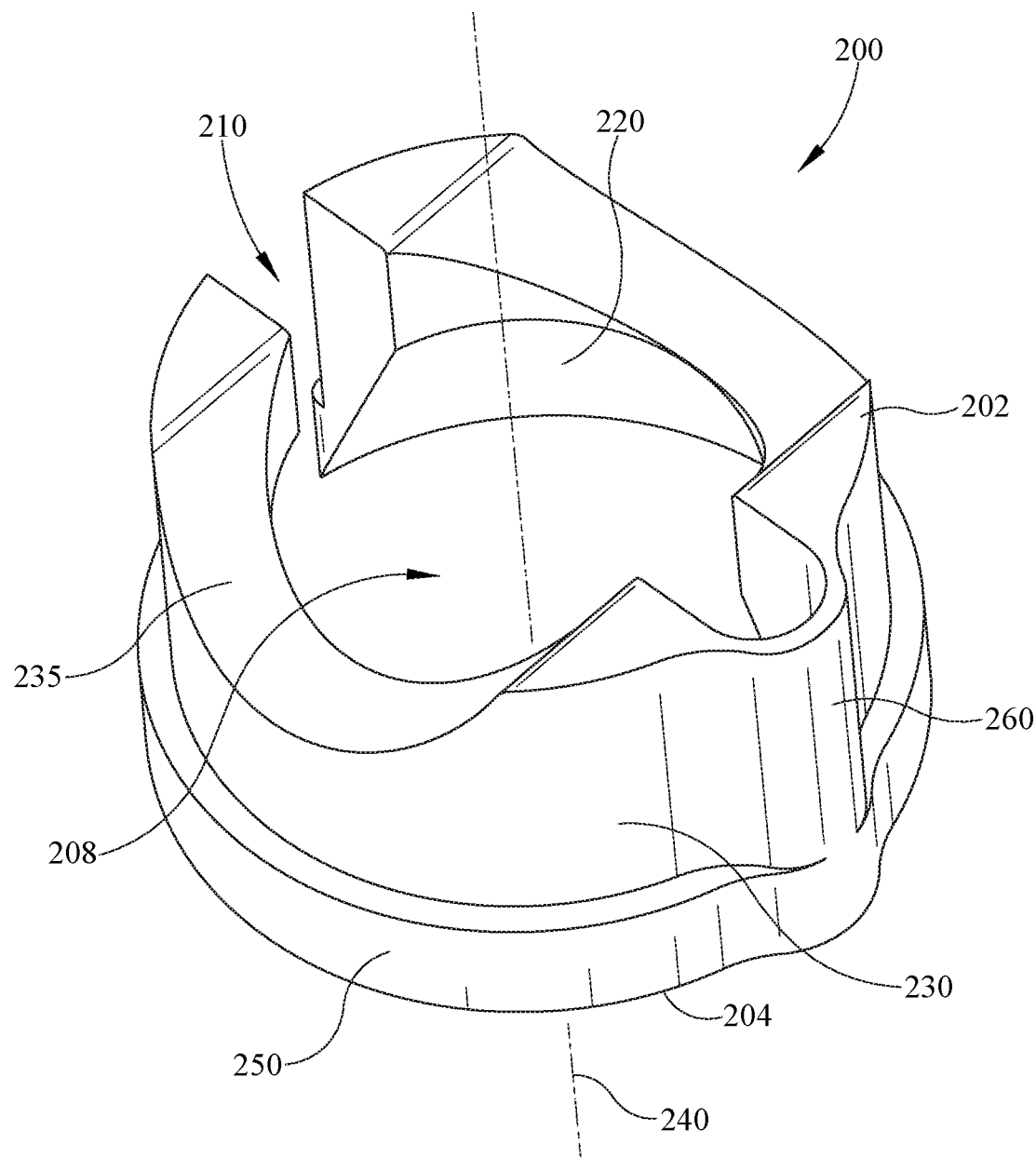
FIG. 2 is a perspective view of an embodiment of a collet for a polyaxial screw assembly described herein.

Turning now to FIG. 2, a first embodiment of a collet 200 for a polyaxial screw assembly is illustrated. Generally, collet 200 may have a ring shape defining a central opening 208 and a longitudinal axis 240. The collet 200 may have a first or top end 202 of the collet 200 and a second or bottom end 204 of the collet 200. The collet 200 longitudinal axis 240 may extend through the center of the collet from a top end 202 to a bottom end 204.

It is further possible that the collet 200 may have a collet interior surface 220 that may be partially spherical and may resemble a portion of the external surface of the screw head 130 thus forming a cradle 235 for receiving a connecting rod. However, the collet interior surface 220 does not need to exactly match the external surface of the screw head 130. More generally, the collet interior surface 220 may be concave with a less tight curvature (that is, a larger radius of curvature) than the spherical portion of the screw head 130. Additionally, in some embodiments, the collet interior surface 220 may be an inverted cone that mates on top of the spherical portion of the screw head 130. The collet interior surface 220 and the screw head 130 may be related to each other such that when the collet 200 is constrained against outward radial deformation, the screw head 130 is prevented from sliding distally with respect to the collet 200, such as by a wedging action.

Figure 4:
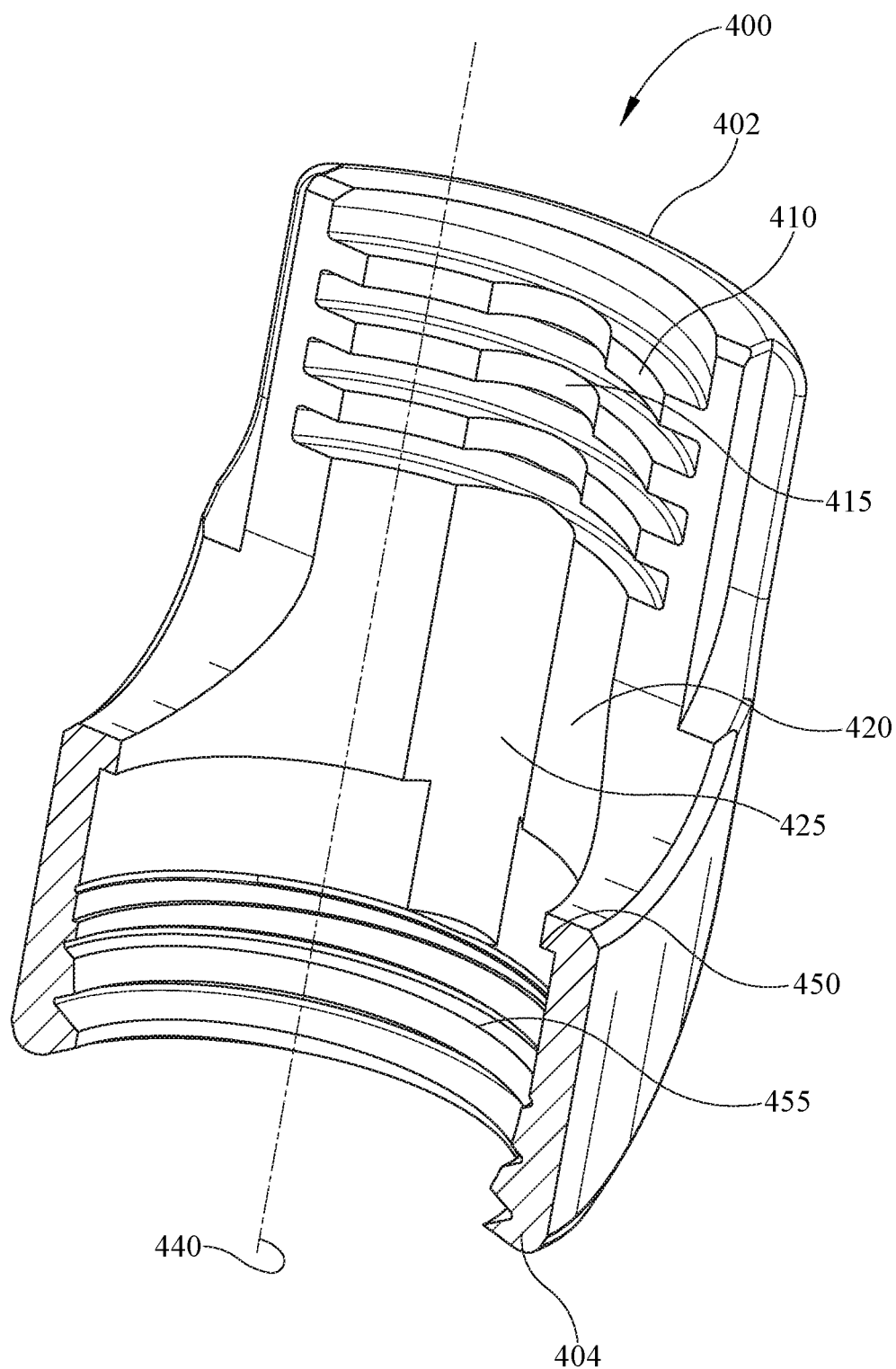
FIG. 4 is a perspective view of a cross-section of an embodiment of a movable head described herein.

It is further possible that the collet 200 may have a collet external surface 230, which may resemble an internal surface 420 of the movable head 400 (see FIG. 4). However, the collet external surface 230 need not exactly match internal surface 420 of movable head 400 or any other internal surface of the movable head 400.

The collet 200 may further include a flexible hinge 260. In some embodiments, the flexible hinge 260 may extend vertically from the top end 202 of the collet 200 towards the bottom end 204 of the collet 200. In some embodiments, such as illustrated in FIG. 2, the flexible hinge 260 may extend fully from the top end 202 to the bottom end 204 of the collet 200. In other embodiments, the flexible hinge 260 may extend vertically from the bottom end 204 of the collet 200 towards the top end 204 of the collet 200. In still other embodiments, the flexible hinge may extend a length between the top end 202 of the collet 200 and the bottom end 204 of the collet 200, for example in a middle area between the top end 202 and the bottom end 204. The collet 200 may further include an open slot 210. In some embodiments, the open slot 210 may be located opposite of the flexible hinge 260, and may fully extend vertically from the top end 202 to the bottom end 204 of the collet 200 creating a discontinuous circumference of the collet 200, but is not so limited.

In some embodiments, the flexible hinge 260 may extend beyond the external surface 230 of the collet 200, such that it protrudes from the remainder of the collet 200. In other embodiments, the flexible hinge 260 may be described as concave in shape extending outward from the exterior surface 230 of the collet.

In some embodiments, the flexible hinge 260 and the open slot 210 are both perpendicular to the cradle 235 for receiving a connecting rod.

The collet 200 may further have an external lip 250 at or near its bottom end. Such an external lip 250 may extend farther outwardly in a radial direction than the rest of the collet 200. The external lip 250 may be interrupted by the open slot 210 just as nearby parts of the collet 200, other than the external lip 250, are interrupted by the open slot 210.

Figure 3:
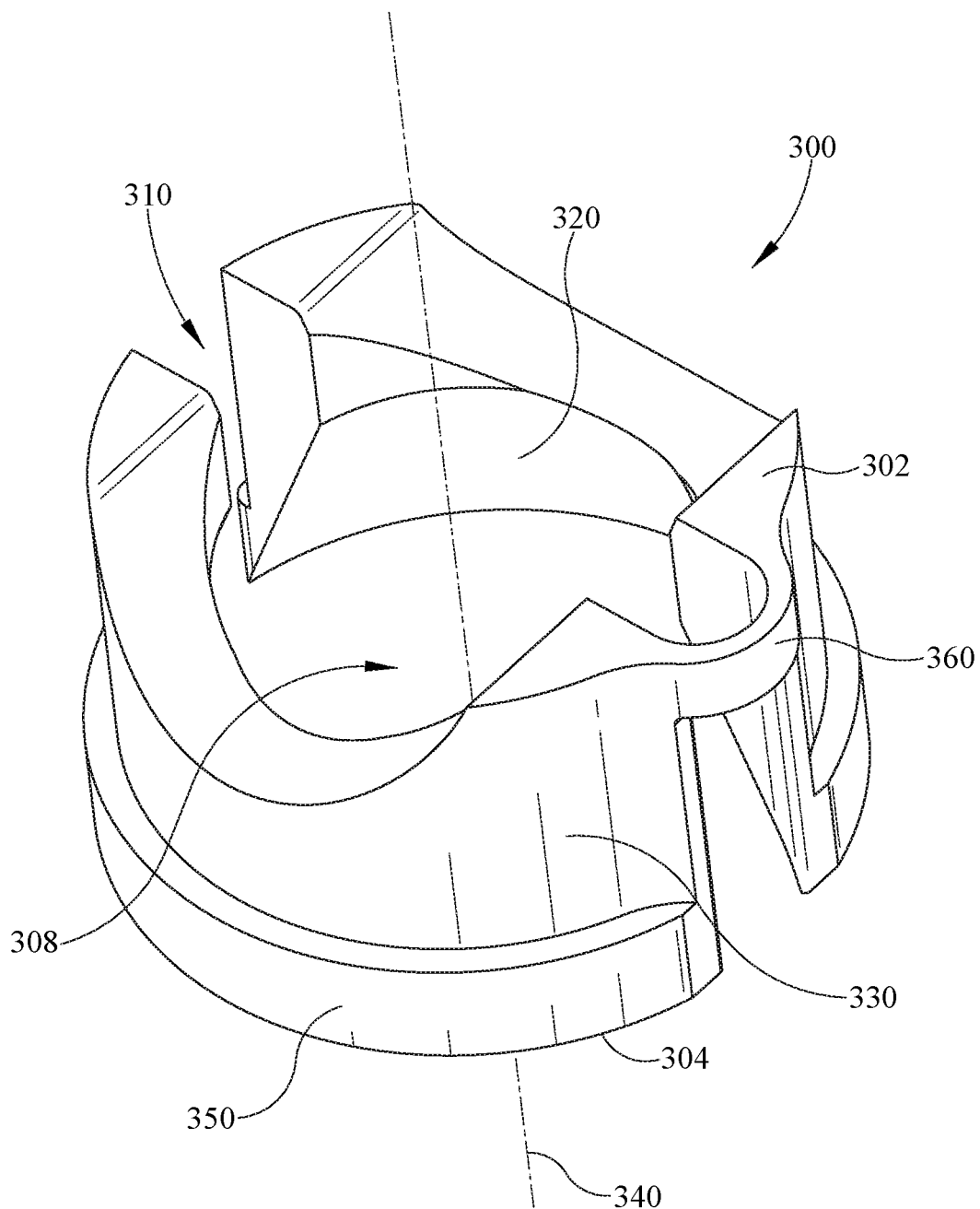
FIG. 3 is a perspective view of another embodiment of a collet for a polyaxial screw assembly described herein.

Turning now to FIG. 3, another embodiment of a collet 300 for a polyaxial screw assembly is illustrated. In many structural aspects, collet 300, illustrated in FIG. 3, is similar to collet 200, illustrated in FIG. 2; as such, similar structures have been numbered with similar numbers, replacing the 2 with a 3. As with collet 200, collet 300 generally may have a ring shape defining a central opening 308 and a longitudinal axis 340. The collet 300 may have a first or top end 302 of the collet 300 and a second or bottom end 304 of the collet 300. The collet 300 longitudinal axis 340 may extend through the center of the collet from a top end 302 to a bottom end 304.

It is further possible that the collet 300 may have a collet interior surface 320 that may be partially spherical and may resemble a portion of the external surface of the screw head 130 thus forming a cradle 335 for receiving a rod. However, the collet interior surface 320 does not need to exactly match the connecting external surface of the screw head 130. More generally, the collet interior surface 320 may be concave with a less tight curvature (that is, a larger radius of curvature) than the spherical portion of the screw head 130. The collet interior surface 320 and the screw head 130 may be related to each other such that when the collet 300 is constrained against outward radial deformation, the screw head 130 is prevented from sliding distally with respect to the collet 300, such as by a wedging action.

Figure 6:
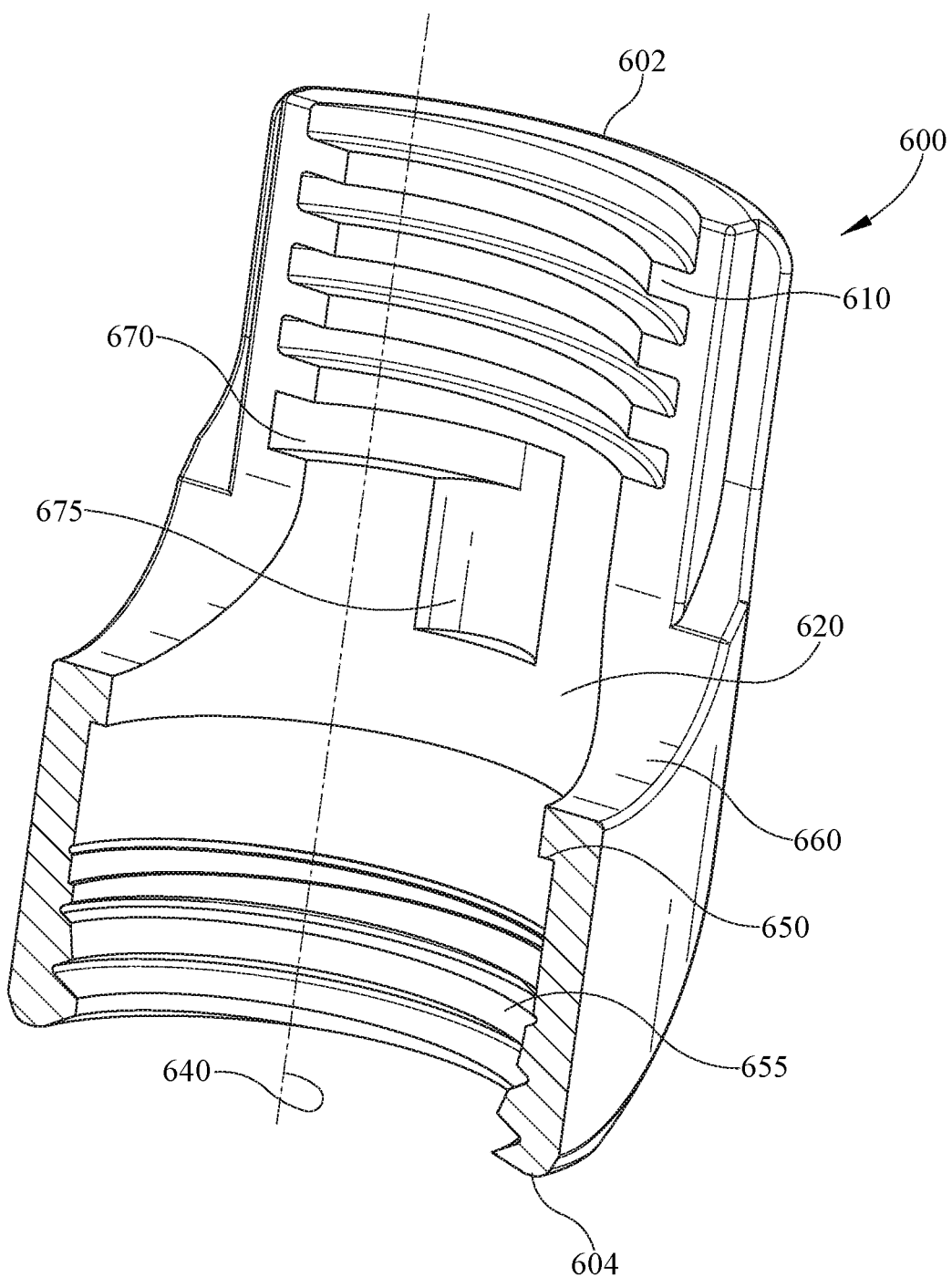
FIG. 6 is a perspective view of a cross-section of an embodiment of a movable head described herein.
Figure 7:
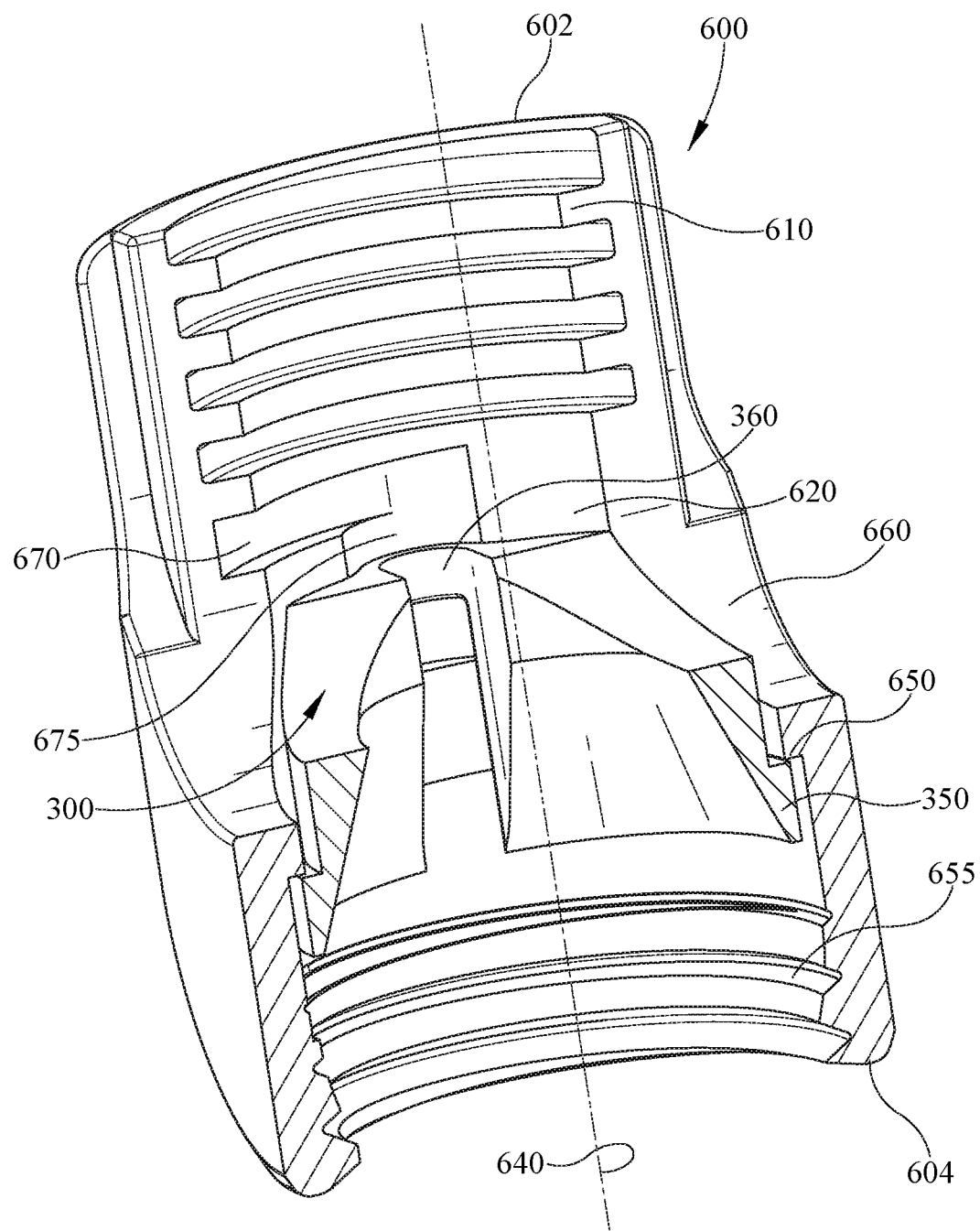
FIG. 7 is a perspective view of a cross-section of the movable head of FIG. 6 with a collet contained therein described herein.

It is further possible that the collet 300 may have a collet external surface 330, which may resemble an internal surface 620 of the movable head 600 (see FIGS. 6 and 7). However, the collet external surface 330 need not exactly match internal surface 620 of movable head 400 or any other internal surface of the movable head 600.

The collet 300 may further include a flexible hinge 360. In some embodiments, the flexible hinge may extend vertically from the top end 302 of the collet 300 towards the bottom end 304 of the collet 300. In other embodiments, such as illustrated in FIG. 3, the flexible hinge 360 may extend from the top end 302 for a distance spaced from the bottom end 304 of the collet 300. In still other embodiments, the flexible hinge 360 may extend a length between the top end 302 of the collet 300 and the bottom end 304 of the collet 300, for example in a middle area between the top end 302 and the bottom end 304. In some embodiments, the flexible hinge 360 may comprise only a small portion of the vertical space between the top end 302 and the bottom end 304 of the collet 300, as illustrated in FIG. 3. In other embodiments, the flexible hinge 360 may comprise a larger portion of the vertical space between the top end 302 and the bottom end 304 of the collet 300. Also similar to collet 200 of FIG. 2, the collet may have an open slot 310. In some embodiments, the open slot 310 may be opposite of the flexible hinge 360, but is not so limited In some embodiments the open slot 310 may extend vertically from the top end 302 to the bottom end 304 of the collet 300, thus creating a discontinuous circumference of the collet 300. In other embodiments, the open slot may partially open the area extending between the top end 302 and the bottom end 304 of the collet 300.

In some embodiments, the flexible hinge 360 may extend beyond the external surface 330 of the collet 300, such that it protrudes from the remainder of the collet 300. In other embodiments, the flexible hinge 360 may be described as concave in shape extending outward from the exterior surface 330 of the collet. In still other embodiments, the flexible hinge 360 may be in the form of a concave tab that extends outward from the external surface 330 of the collet 300.

In some embodiments, the flexible hinge 360 and the open slot 310 are both perpendicular to the cradle 335 for receiving a connecting rod.

The collet 300 may further have an external lip 350 at or near its bottom end. Such an external lip 350 may extend farther outwardly in a radial direction than the rest of the collet 300. The external lip 350 may be interrupted by the open slot 310 just as nearby parts of the collet 300, other than the external lip 350, are interrupted by the open slot 310.

The various embodiments of the collet described herein may function similarly to each other. Generally, the collet 200, 300 may be capable of expanding and deforming radially outwardly so as to receive the bone screw screw head 130. This radial expansion and deformation may be primarily at the open slot 210, 310, which may splay open when axial compression force is transferred to the collet 200, 300 through the set screw and connecting rod. Furthermore the radial expansion and deformation of the collet 200, 300 may minimize the axial compression force that is transferred to the screw head 130.

Movable Head

Figure 5:
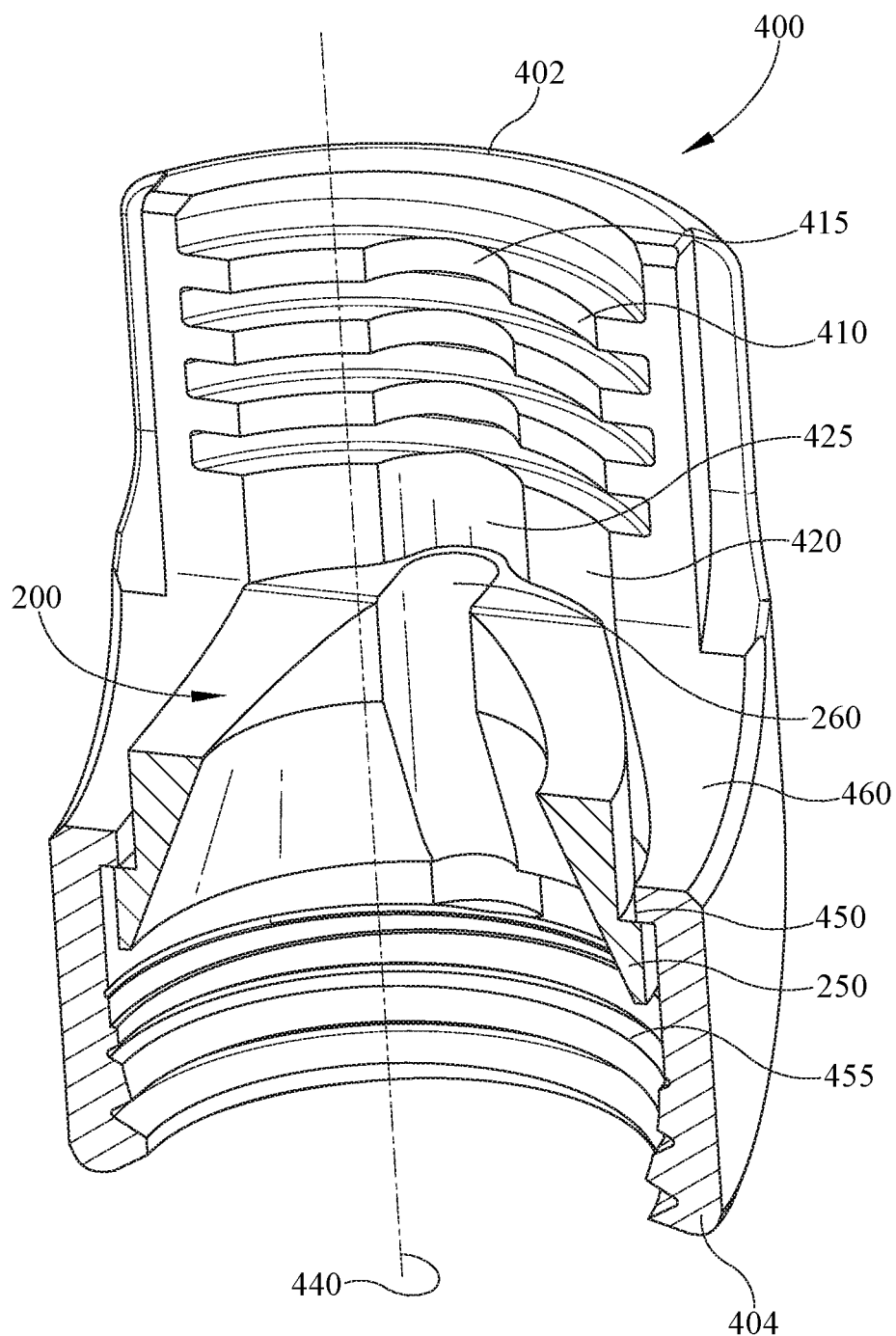
FIG. 5 is a perspective view of a cross-section of the movable head of FIG. 4 with a collet contained therein

Turning now to FIGS. 4-8D, multiple embodiments of a movable heads consistent with the disclosure herein are described and illustrated. In particular, FIGS. 4 and 5 illustrate an embodiment of a movable head 400 for use with the particular embodiment of collet 200 illustrated in FIG. 2; however this is not to be understood as limiting, as the embodiment of movable head 400 illustrated in FIGS. 4 and 5 may be utilized with collet 300, or other embodiments of a collet.

Referring now to FIGS. 4 and 5, movable head 400 may have a proximal end 402 and a distal end 404 and a generally longitudinal axis 440 extending from the proximal end 402 to the distal end 404 through the center of the movable head 400. The movable head 400 may also have a first or top portion or end and a second or bottom portion or end, whereby the top portion is located at a proximal end 402 of the movable head 400 and the bottom portion is located at a distal end 404 of the movable head 400. The movable head 400 may also have, at its proximal end 402, a U-shaped passageway or U-trough 460 through the movable head 400, only half of which is visible in FIGS. 4 and 5. The U-trough 460 may have an axis generally perpendicular to the longitudinal axis 440 of the movable head. The U-trough 460 axis may also be generally transverse through the movable head 400. The movable head 400 may have a hole (not illustrated in FIGS. 4 and 5) therethrough at its distal end or bottom portion, through which the screw 105, or portions thereof, may pass.

In some embodiments, the movable head 400 may have a first set of internal threads 410 at its proximal end 402. This first set of internal threads 410 may be capable of receiving a set screw 500. In some embodiments, the first set of internal threads 410 may have a roughly semi-circular or concave-shaped cutout, indention, or track 415. In some embodiments, this track may traverse the internal threads from the top to the bottom. In other embodiments, this track may be described as a channel that traverses the internal surface of the movable head. In some embodiments, these cutouts, indentions, or track 415 may be shaped so as receive the flexible hinge 260, 360 of the collet 200, 300 when the collet 200, 300 is in an unexpanded and undistorted state.

The movable head 400 may also have an internal surface 420 located between the first set of internal threads 410 and the hole (not illustrated) at the distal end 404. The internal surface 420 may be generally concave and may be at least partially cylindrical or generally spheroidal in shape. Similar to the first set of threads 415, the internal surface may also have a roughly semi-circular or concave-shaped cutout, intention, or track 425. In some embodiments, this cutout, indention, or track 425 in the internal surface 420 may be shaped so as receive the flexible hinge 260, 360 of the collet 200, 300 when the collet 200, 300 is in an unexpanded state.

The movable head 400 may also have an internal lip 450 between the internal surface 420 and a second set of internal threads 455, which may function to retain a lower lip of a collet after installation.

FIG. 5 illustrates the movable head 400 with collet 200 inserted. The collet 200 may be inserted into the movable head 400 from an opening at the top (not illustrated) of the movable head 400 or through an opening defined by the U-trough 460. The collet 200 may then be positioned such that the flexible hinge 260 is aligned with the cutouts or indentions 415 of the first set of internal threads 410. The collet may then to move vertically towards the distal end 404 of the movable head. The flexible hinge 260 of the collet 200 may pass through the cutouts or indentions 415 of the first set of internal threads 410 into the cutout or intention 425 of the internal surface 420 as the collet 200 moves toward the distal end 404.

Generally, the collet 200 may be inserted into the moveable head 400 in a compressed, undistorted state; this may also be described as a "pinched" state. The collet 200 may continue its vertical movement towards the distal end, and the external lip 250 at or near the bottom end of the collet 200 may engage the internal lip 450 of the movable head 400, which is positioned between the internal surface 420 and the distal end 404. In some embodiments, there may be a second set of internal threads 455 located proximate the distal end 404. Once the collet 200 has engaged the internal lip 450 of the movable head 400, the collet 200 may expand radially outwardly in order to interfere with internal lip 450 and prevent ejection. After installation, in some embodiments, in order to receive the screw head 130 radial expansion and deformation of the collet 200 may occur primarily at the open slot 210, which may splay open when axial compression force is transferred to the top end 202 of the collet 200, through the set screw 500 and connecting rod. Furthermore, this radial expansion and deformation of the collet 200 (e.g. by splaying open the open slot 210) may absorb at least a portion of the force that would have otherwise been transferred to screw head 130, thus minimizing the axial compression force that is transferred to the screw head 130, which may prevent failure of the screw head/bone screw interface. In some embodiments, the minimization the axial compression force transferred to the screw head 130 may prevent the second set of internal threads 455 (if present) of movable head 400 from being stripped or sheared.

Turning now to FIGS. 6 and 7, another embodiment of a movable head 600 is illustrated. In some embodiments, movable head 600 may be used with the particular embodiment of collet 300 illustrated in FIG. 3; however this is not to be understood as limiting, as the embodiment of movable head 600 illustrated in FIGS. 6, 7, and 8A-D may be utilized with other embodiments of a collet.

Referring now to FIG. 6, a perspective view of a cross-section of an embodiment of a movable head 600 is illustrated. The movable head 600 may have a proximal end 602 and a distal end 604 and a generally longitudinal axis 640 extending from the proximal end 602 to the distal end 604 through the center of the movable head 600. The movable head 600 may also have a first or top portion or end and a second or bottom portion or end, whereby the top portion is located at a proximal end 602 of the movable head 600 and the bottom portion is located at a distal end 604 of the movable head 600. The movable head 600 may also have, at its proximal end 602, a U-shaped passageway or U-trough 660 through the movable head 600 (only half of which is visible in FIGS. 6 and 7; see FIGS. 8A-D). The U-trough 660 may have an axis generally perpendicular to the longitudinal axis 640 of the movable head. The U-trough 660 axis may also be generally transverse through the movable head 600. The movable head 600 may have a hole (not illustrated in FIGS. 6 and 7) therethrough at its distal end or bottom portion, through which the screw 105, or portions thereof, may pass.

The movable head 600 may have a first set of internal threads 610 at its proximal end 602. This first set of internal threads 610 may be capable of receiving a set screw 500 (see FIG. 1). The movable head 600 may further have an internal surface 620 located between the first set of internal threads 610 and the hole (not illustrated) at the distal end 604. The internal surface 620 may be generally concave and may be at least partially spherical or generally spheroidal in shape. The movable head 600 may also have an internal lip 650 between the internal surface 620 and a second set of internal threads 655.

The internal surface 620 may further comprise a first track 670. In some embodiments, this track 670 is located generally parallel to the first set of internal threads 610 and the second set of internal threads 655 (if present). In some embodiments, the first track 670 may be aa channel shaped so as to receive a flexible hinge of a collet, and as such the width and depth of the first track 670 may appropriately correspond, or be slightly larger than, the width and depth of a flexible hinge of a collet, for example flexible hinge 360. The internal surface 620 may also comprise a second track 675, which intersects the first track 670, such that the first track 670 and second track 675 are roughly perpendicular to each other, such that the first track 670 and the second track 675 form a roughly 90 degree angle. In some embodiments, the second track 675 may also be shaped so as to receive a flexible hinge of a collet, and as such the width and depth of the second track 675 may also appropriately correspond, or be slightly larger than, the width and depth of a flexible hinge of a collet, for example flexible hinge 360. In other embodiments, the width of the second track 675 may be substantially larger than the width of a flexible hinge, for example flexible hinge 360.

FIG. 7 illustrates the movable head 600 with collet 300 in an installed position. Generally, the collet 300 may be inserted into the moveable head 600 in a compressed state; this may also be described as a "pinched" state. The installation of the collet 300 into the movable head 600 is described in detail below with respect to FIGS. 8A-D. However, as illustrated in FIG. 7, once the collet 300 has been installed in its final orientation the collet 300 may engage the internal lip 650 of the movable head 600, the collet 300 may expand and deform radially outwardly in order to receive the screw head 130. In some embodiments, this radial expansion and deformation of the collet 300 may occur primarily at the open slot 310, which may splay open when axial compression force is transferred to the top end 302 of the collet 300, through the set screw 500 and connecting rod. In other embodiments, this radial expansion and deformation of the collet 300 may occur at both the open slot 310 and the flexible hinge 360. Furthermore, this radial expansion, deformation of the collet 300 (e.g. by splaying open the open slot 310 and/or the flexible hinge 360), and wedging of the components together may absorb at least a portion of the force that would have otherwise been transferred to screw head 130, thus minimizing the axial compression force that is transferred to the screw head 130. In embodiments, with a second set of internal threads 655 of movable head 600, this may prevent or minimize these internal threads 655 from being stripped or sheared.

FIGS. 8A-D illustrate the movable head 600 with a collet 300 contained therein in various positions for installation. Starting with FIG. 8A, a collet 300 is illustrated in an initial installation position, or in a first orientation. In such a position, the collet 300 is inserted into the movable head 600. In some embodiments, the collet 300 is inserted through the U-trough 660. The initial installation position, or first orientation, may align the collet 300 so that a first edge of the collet 312 intersects the first track 670 of the movable head 600. The collet 300 may then be moved from the installation position to an engaged position (illustrated in FIG. 8B). In some embodiments, the movement from the installation position to the engaged position may be through rotation of the collet 300.

Figure 8A:
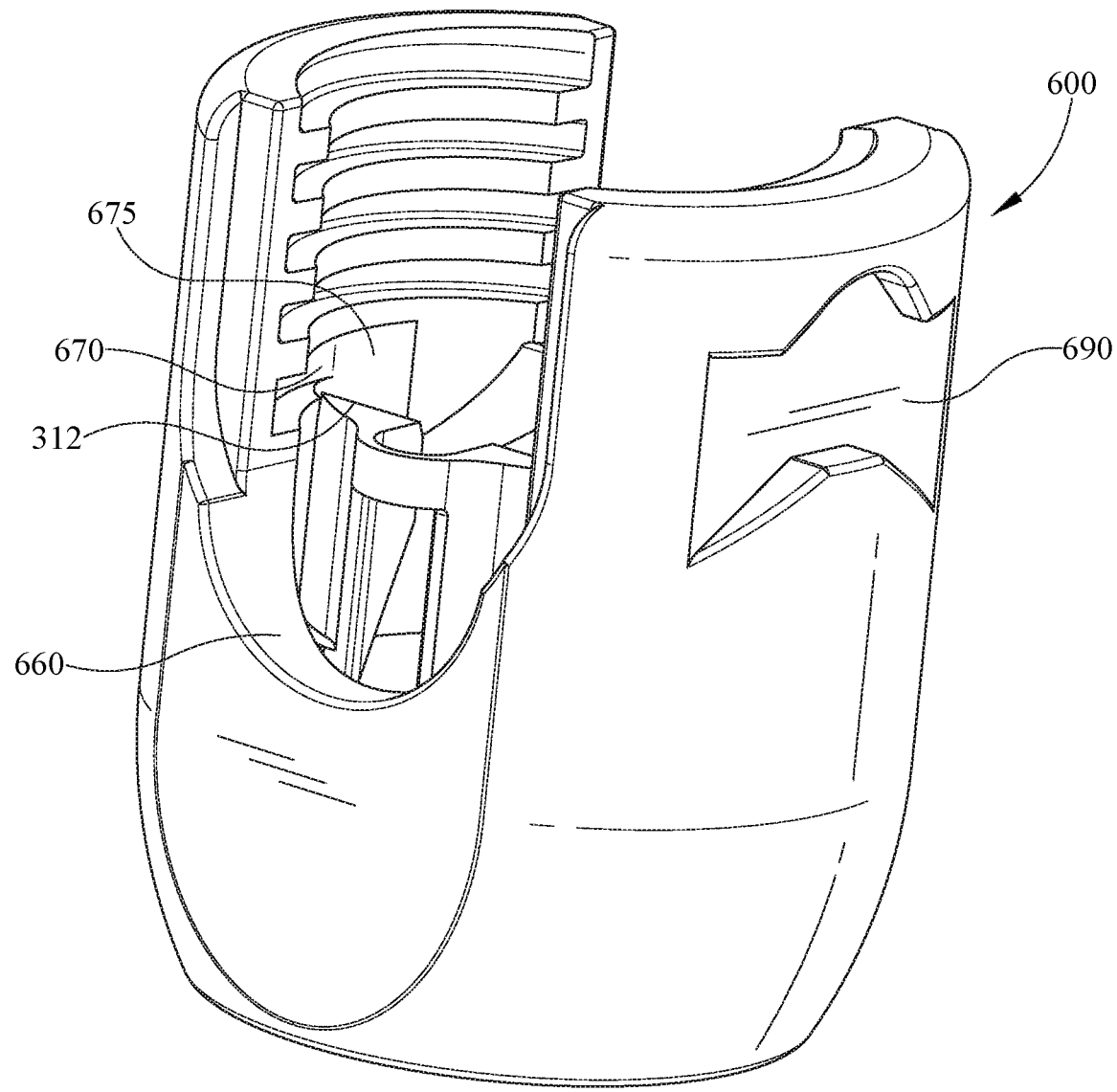
FIG. 8A-D are perspective views of the movable head of FIG. 6 with a collet contained therein in various positions for installation.
Figure 8B:
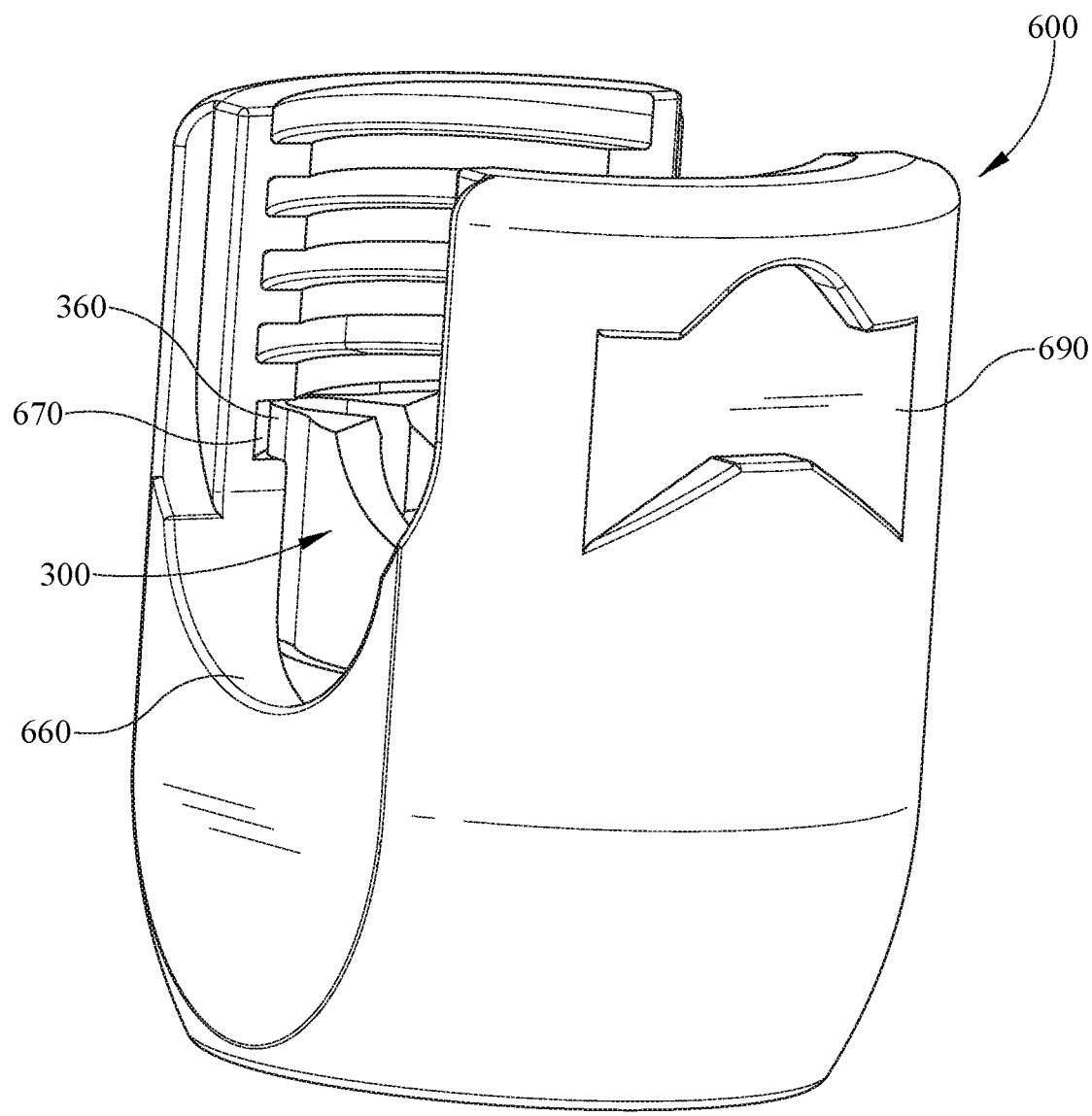
Figure 8C:
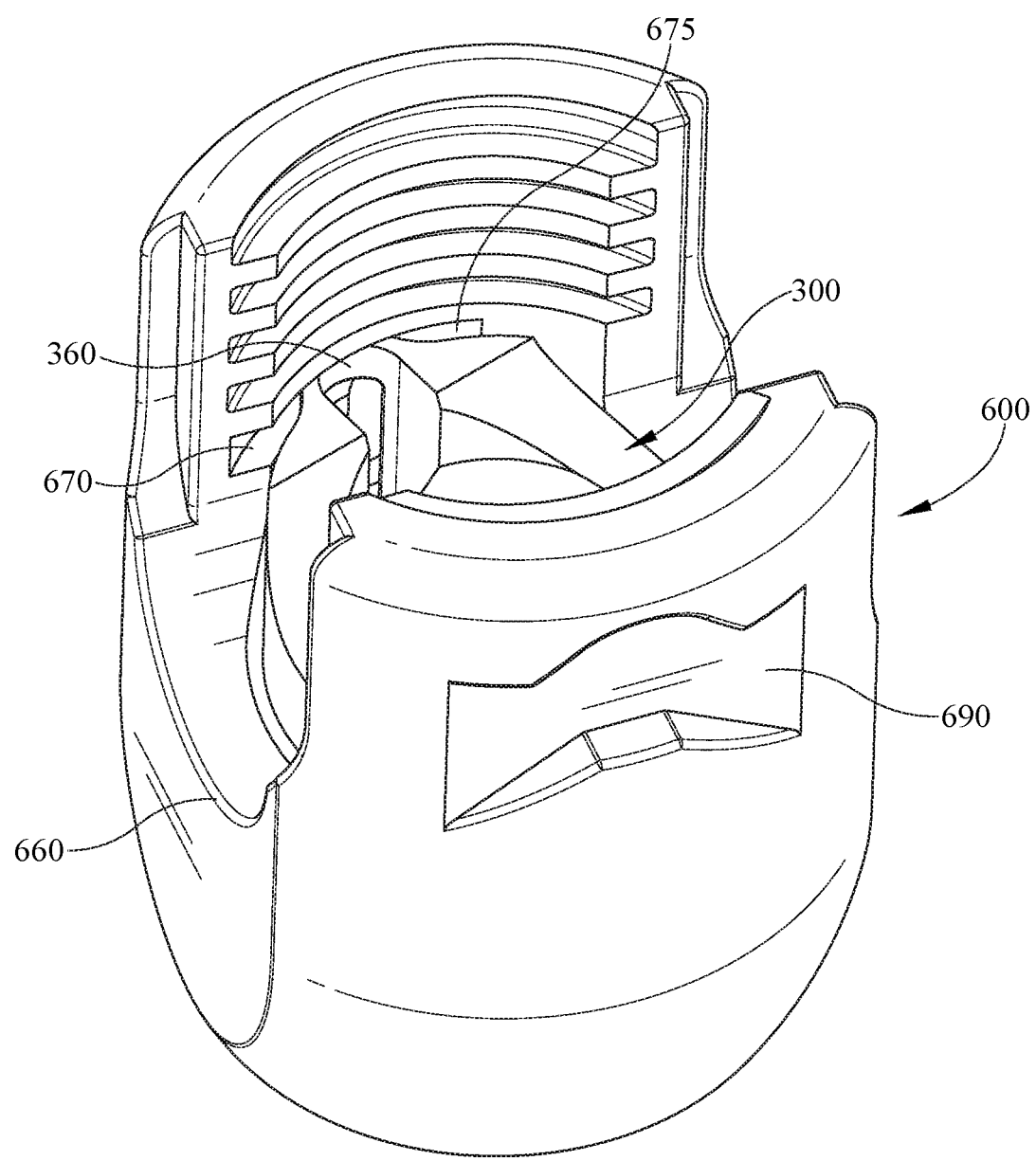

FIG. 8B illustrates the collet 300 in the movable head 600 in the engaged position, or in a second orientation. In the engaged position, the flexible hinge 360 may be inserted into the first track 670 of the movable head 600, in some case by rotation of the collet 300. FIG. 8C illustrates the collet 300 in a rotated position, wherein the flexible hinge 360 may be moved along, or through, the first track 670. The collet 300 may then be moved from the rotated position to an installed position (illustrated in FIG. 8D) through movement along the second track 675 of the movable head 600. Throughout installation, as depicted in FIGS. 8A-C, the collet 300 is in a compressed/pinched position, as described previously.

Figure 8D:
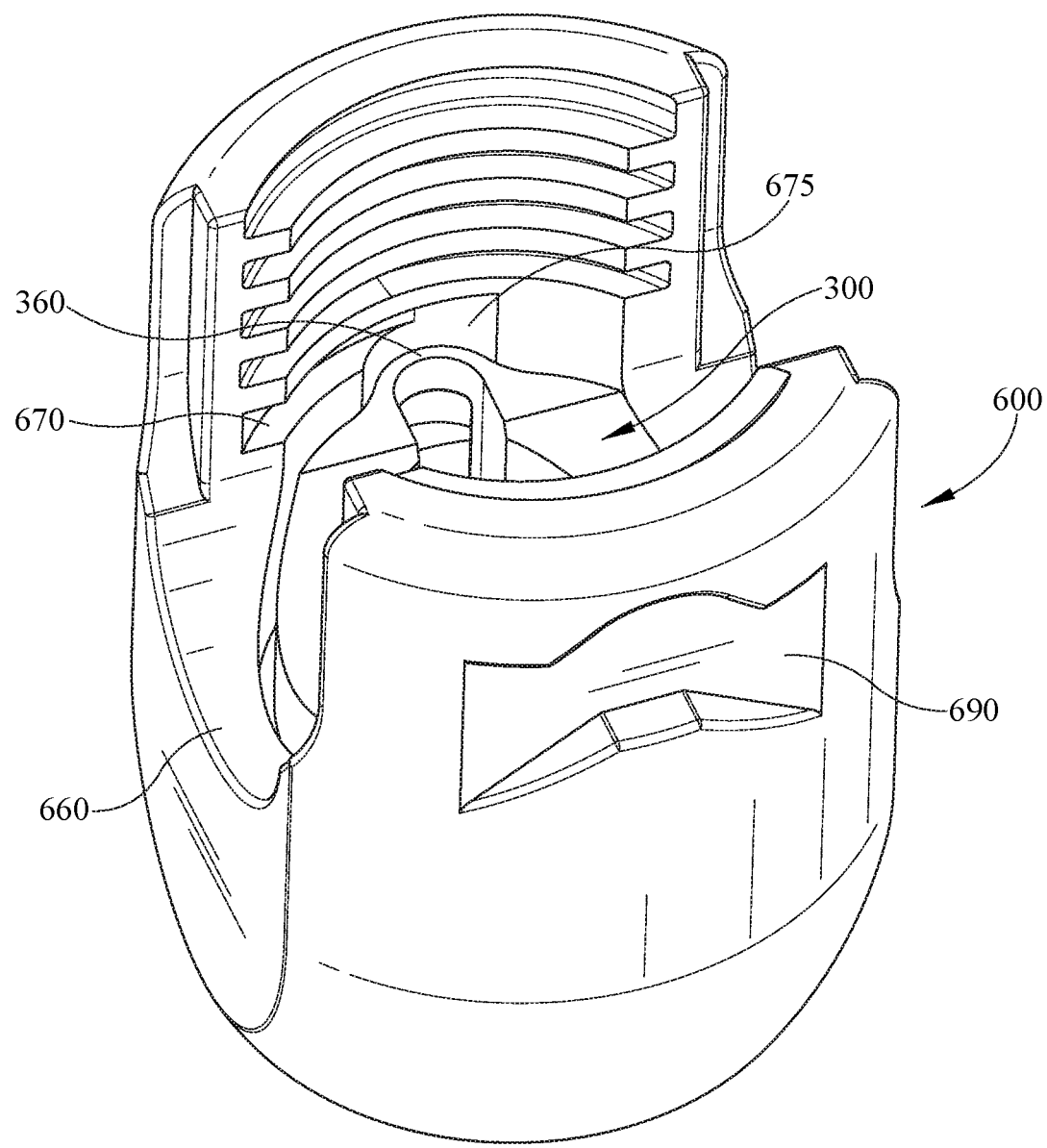

FIG. 8D illustrates the collet 300 in an installed position. As discussed previously, the collet 300 may be moved (e.g. by rotation) along the first track 670 of the movable head 600 until the first track 670 intersects the second track 675. When the first track 670 intersects the second track 675 the collet 300 may engage the second track 675. In some embodiments, this engagement of the second track 675 means the collet may move in a direction approximately 90 degrees from the direction the collet 300 moved along the first track 675. In other embodiments, this engagement of the second track 675 may cause the collet 300 to move in a vertical direction (as opposed to the horizontal direction of the movement along the first track 670). In still other embodiments, the engagement of the second track may cause the collet to move in a horizontal direction (as opposed to a vertical direction of the movement along the first track) (not illustrated in FIGS. 8A-D).

Once in an installed position, the collet 300 may spring back from a compressed or pinched position to an uncompressed state; the collet 300 may then be deformed outward to accept the bone screw 105. During locking, the collet 300 may expand or deform around the bone screw 105, and wedge against the screw head 130. The external lip 350 of the collet 300 may also engage the internal lip 650 of the movable head 600 (see FIG. 7). As discussed with respect to FIG. 7, once the collet 300 has engaged the internal lip 650 of the movable head 600, the collet 300 may expand and deform radially outwardly in order to receive the screw head 130. In some embodiments, this radial expansion and deformation of the collet 300 may occur primarily at the open slot 310, which may splay open when axial compression force is transferred to the top end 302 of the collet 300, through the set screw 500 and connecting rod, and may contact the internal surface 650 of the screw head which may absorb at least a portion of the force that would have otherwise been transferred to screw head 130 by wedging the components together, thus minimizing the axial compression force that is transferred to the screw head 130. Minimizing the axial compression force that is transferred to the screw head 130 may prevent the second set of internal threads 655 of movable head 600 from being stripped or sheared.

Although the installation of the collet 300 into a movable head 600 is described in terms of the collet 300 moving, this is not to be understood as limiting. In some embodiments, the movable head 600 may move relative to the collet 300.

The movable head 400, 600 may further include, on an external surface, any of a variety of interface features. Although referenced and illustrated with respect to movable head 600, this is not intended to be limiting, as movable head 400, or any other movable head may also include interface features. For example, interface features 690, which may have a corresponding interface feature directly opposed from it (not illustrated in FIG. 8A-D), may be utilized for interfacing with a tool or instrument. The interface features 690 may be identical to each other or symmetrical to each other about a common plane or axis, or, alternatively, there may be design differences between the interface features. It is possible that either or both of the interface features 690 may have an undercut so as to provide a slip-resistant interface with the instrument or tool. As is illustrated most particularly in FIG. 8B, such an undercut may have a cross-sectional shape that is trapezoidal.

While several embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The foregoing description of several embodiments of the invention has been presented for purposes of illustration. It is not intended to be exhaustive or to limit the invention to the precise steps and/or forms disclosed, and obviously many modifications and variations are possible in light of the above teaching.

The invention claimed is:

1. An apparatus, comprising:
   a screw, comprising a shaft and a screw head fixedly attached with the shaft, wherein the screw head further comprises a portion of a sphere;
   a movable head comprising a top portion and a bottom portion, a concave interior larger than the screw head, and being movable with respect to the screw head;
   a connecting rod;
   a locking element, capable of engaging the movable head and creating an axial compression force on the connecting rod; and
   a collet having a central opening with a longitudinal axis, wherein the collet is interposed between the screw head and the concave interior of the movable head,
   wherein the collet comprises a top portion capable of contacting said connecting rod, and at least one flexible hinge, wherein the at least one flexible hinge extends from the top portion of the collet and for a distance spaced from the bottom portion of the collet and includes a concave interior intersecting the central opening and extending radially outward away from the central opening and the longitudinal axis whereby the concave interior of the at least one flexible hinge faces towards the longitudinal axis, and wherein the collet includes one or more open slots extending in a direction between the top portion of the collet and the bottom portion of the collet.

2. The apparatus of claim 1, wherein the collet further comprises an external surface, and wherein the at least one flexible hinge has a convex exterior opposite to the concave interior at a larger radius from the central axis of the collet than the external surface of the collet.

3. The apparatus of claim 2, wherein the concave interior of the at least one flexible hinge extends radially outward beyond the external surface of the collet.

4. The apparatus of claim 1, wherein the at least one flexible hinge is opposite to the one more open slots.

5. The apparatus of claim 1, wherein the movable head further comprises one or more tracks capable of receiving the at least one flexible hinge of the collet.

6. The apparatus of claim 5, where the one or more tracks are vertical tracks.

7. The apparatus of claim 6, where the one or more tracks are circumferential tracks.

8. A collet for a polyaxial screw assembly, comprising:
   a top end configured to receive a connecting rod;
   a bottom end configured to interface with a screw head;
   a central opening with a longitudinal axis extending between the top end and the bottom end; and
   one or more flexible hinges, wherein the one or more flexible hinges extend from the top end of the collet and for a distance spaced from the bottom end of the collet and includes a concave interior intersecting the central opening and extending radially outward away from the central opening and the longitudinal axis whereby the concave interior of the one or more flexible hinges faces towards the longitudinal axis.

9. The collet of claim 8, wherein the one or more flexible hinges comprises a convex exterior opposite the concave interior extending outward from an external surface of the collet.

10. The collet of claim 8, wherein the one or more flexible hinges is at a position that is perpendicular to a longitudinal axis of a cradle of the top end capable of receiving the connecting rod.

11. The collet of claim 8, further comprising one or more open slots extending in a direction between the top end and the bottom end, wherein the one or more open slots creates a discontinuous circumference of the collet.

12. A method of inserting a collet into a movable head, the method comprising:
   obtaining a movable head, wherein the movable head includes one or more tracks;
   obtaining a collet, wherein the collet includes a central opening with a longitudinal axis and one or more flexible hinges, and wherein the one or more flexible hinges includes a concave interior intersecting the central opening and extending radially outward away from the central opening and the longitudinal axis whereby the concave interior of the one or more flexible hinges faces towards the longitudinal axis;

inserting the one or more flexible hinges of the collet into the one or more tracks of the movable head when the collet is in a compressed configuration;

moving the collet in the compressed configuration along the one or more tracks of the movable head by sliding the one or more flexible hinges in the one or more tracks; and positioning the collet into an uncompressed configuration within said moveable head.

13. The method of claim 12, wherein the one or more tracks includes a first track intersecting a second track, wherein the second track is substantially circumferential and the first track is traverse to the second track.

14. The method of claim 13, wherein moving the collet includes rotating the collet from a first orientation to a second orientation within the second track.

15. The method of claim 13, wherein the first track is a channel and the second track is a channel, and wherein the step of moving the collet includes circumferentially sliding the one or more flexible hinges in the second track before axially sliding the one or more flexible hinges in the first track.

16. The method of claim 12, wherein the collet further comprises one or more open slots extending in a direction between a top end and a bottom end of the collet, wherein the one or more open slots creates a discontinuous circumference of the collet.

\* \* \* \* \*